(12) United States Patent
Stetson et al.

(10) Patent No.: US 8,251,511 B2
(45) Date of Patent: Aug. 28, 2012

(54) METHOD FOR FINDING THE LATERAL POSITION OF THE FOVEA IN AN SDOCT IMAGE VOLUME

(75) Inventors: Paul F. Stetson, Piedmont, CA (US); Homayoun Bagherinia, San Francisco, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 0 days.

(21) Appl. No.: 13/299,962

(22) Filed: Nov. 18, 2011

(65) Prior Publication Data

US 2012/0062841 A1    Mar. 15, 2012

Related U.S. Application Data

(63) Continuation of application No. 12/415,976, filed on Mar. 31, 2009, now Pat. No. 8,079,711.

(60) Provisional application No. 61/047,525, filed on Apr. 24, 2008.

(51) Int. Cl.
*A61B 3/00* (2006.01)
*A61B 3/10* (2006.01)

(52) U.S. Cl. ........................ 351/246; 351/205

(58) Field of Classification Search ........... 351/246, 351/205, 208–210, 212; 385/1–3, 40, 129–132, 385/5, 8–9; 359/315, 215, 247, 251–252, 359/254, 108, 237–238, 278–279, 290–292, 359/298, 300–302

See application file for complete search history.

(56) References Cited

U.S. PATENT DOCUMENTS

| 5,321,501 A | 6/1994 | Swanson et al. |
| 5,633,974 A | 5/1997 | Chia |
| 7,301,644 B2 | 11/2007 | Knighton et al. |
| 2007/0291277 A1 | 12/2007 | Everett et al. |
| 2009/0196477 A1* | 8/2009 | Cense et al. ............... 382/131 |
| 2009/0257636 A1* | 10/2009 | Wei et al. ............... 382/131 |

OTHER PUBLICATIONS

Final Office Action received for U.S. Appl. No. 12/415,976, mailed on Aug. 5, 2011, 11 pages.
Choma et al., "Sensitivity Advantage of Swept Source and Fourier Domain Optical Coherence Tomography", Optics Express, vol. 11, No. 18, Sep. 8, 2003, pp. 2183-2189.
De Boer et al., "Improved Signal-to-Noise Ratio in Spectral-Domain Compared with Time-Domain Optical Coherence Tomography", Optics Letters, vol. 28, No. 21, Nov. 1, 2003, pp. 2067-2069.
Frangi et al., "Model-Based Quantitation of 3-D Magnetic Resonance Angiographic Images", IEEE Transactions on Medical Imaging, vol. 18, No. 10, Oct. 1999, pp. 946-956.
Hausler et al., "'Coherence Radar' and 'Spectral Radar'-New Tools for Dermatological Diagnosis", Journal of Biomedical Optics, vol. 3, No. 1, Jan. 1998, pp. 21-31.
Hitzenberger et al., "In Vivo Intraocular Ranging by Wavelength Tuning Interferometry", SPIE, vol. 3251, 1998, pp. 47-51.
Leitgeb et al., "Performance of Fourier Domain Vs. Time Domain Optical Coherence Tomography", Optics Express, vol. 11, No. 8, Apr. 21, 2003, pp. 889-894.

(Continued)

*Primary Examiner* — Dawayne A Pinkney
(74) *Attorney, Agent, or Firm* — Morrison & Foerster LLP

(57) ABSTRACT

Embodiments of the present invention provide methods for finding the lateral position of the fovea in an OCT image volume. In one instance, a cost function is developed whose minimum is located at or near the foveal center. This cost function includes one or more measures of retinal layer thickness and/or measures of distance from blood vessels or a priori locations.

22 Claims, 5 Drawing Sheets

OTHER PUBLICATIONS

Li et al., "Automated Detection of the Retinal Blood Vessels and Fovea for Scanning Laser Tomography Images", Invest. Ophthalmol. Vis. Sci., vol. 48, E-Abstract 2605, 2007, 1 page.

Narasimha-Iyer et al., "Robust Detection and Classification of Longitudinal Changes in Color Retinal Fundus Images for Monitoring Diabetic Retinopathy", IEEE Transactions on Biomedical Engineering, vol. 53, No. 6, Jun. 2006, pp. 1-15.

Niemeijer et al., "Automatic Detection of the Optic Disc, Fovea and Vascular Arch in Digital Color Photographs of the Retina", Proceedings of the British Machine Vision Conference, 2005, pp. 109-118.

Niemeijer et al., "Segmentation of the Optic Disc, Macula and Vascular Arch in Fundus Photographs", IEEE Transactions on Medical Imaging, vol. 26, No. 1, Jan. 2007, pp. 116-127.

Non-Final Office Action received for U.S. Appl. No. 12/415,976, mailed on Feb. 15, 2011, 10 pages.

Notice of Allowance received for U.S. Appl. No. 12/415,976, mailed on Aug. 22, 2011, 9 pages.

Sato et al., "Three-Dimensional Multi-Scale Line Filter for Segmentation and Visualization of Curvilinear Structures in Medical Images", Medical Image Analysis, vol. 2, No. 2, 1998, pp. 143-168.

* cited by examiner

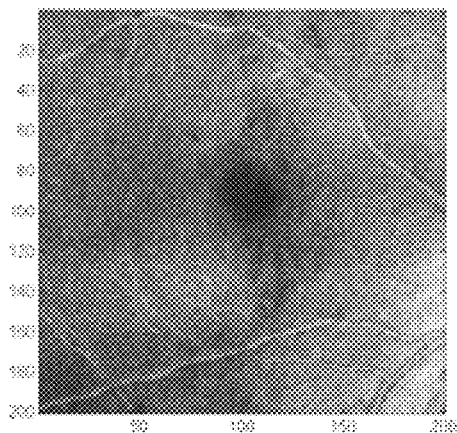
Fig. 6 (a) an ILM slab
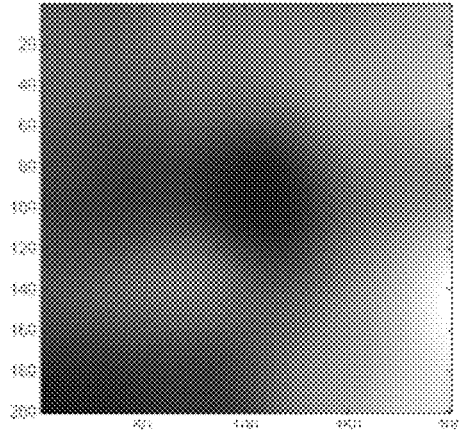
Fig. 6 (b) the ILM slab reflectivity component of the cost function
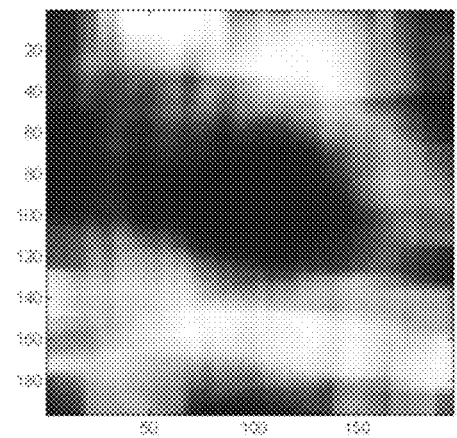
Fig. 6 (c) the blood vessel component of the cost function
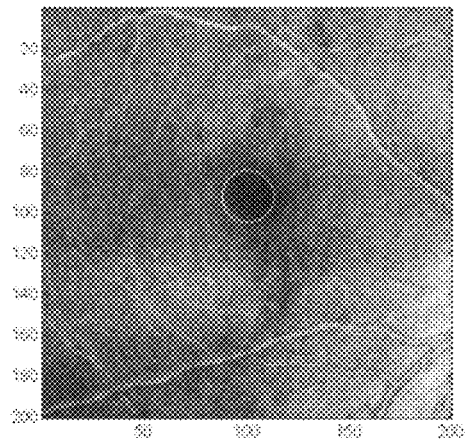
Fig. 6 (d) the automatically detected fovea

METHOD FOR FINDING THE LATERAL POSITION OF THE FOVEA IN AN SDOCT IMAGE VOLUME

CROSS-REFERENCE TO RELATED APPLICATIONS

This application is a continuation of U.S. application Ser. No. 12/415,976 filed Mar. 31, 2009 which in turn claims the benefit of the filing date under 35 U.S.C. §119(e) of Provisional U.S. Patent Application Ser. No. 61/047,525, filed on Apr. 24, 2008, the disclosure of which is hereby incorporated by reference in its entirety.

TECHNICAL FIELD

The present invention relates to medical imaging, and in particular to systems that are adapted to displaying views of Optical Coherence Tomography ("OCT") data.

BACKGROUND

Optical Coherence Tomography (OCT) is an optical imaging technology for performing in situ real time high-resolution cross sectional imaging of tissue structures at a resolution of less than 10 microns. In recent years, it has been demonstrated that Fourier domain OCT (FD-OCT) has significant advantages in both speed and signal-to-noise ratio as compared to time domain OCT (TD-OCT). (Leitgeb, R. A., et al., *Optics Express* 11:889-894; de Boer, J. F. et al., *Optics Letters* 28: 2067-2069; Choma, M. A., and M. V. Sarunic, *Optics Express* 11: 2183-2189). The primary implementations of FD-OCT employ either a wavelength swept source and a single detector (Hitzenberger, C. K., et al. (1998) *In-vivo intraocular ranging by wavelength tuning interferometry. Coherence Domain Optical Methods in Biomedical Science and Clinical Applications II, SPIE*) or a broadband source and an array spectrometer (Häusler, G. and M. W. Lindner (1998). "*Coherence Radar*" and "*Spectral Radar*"—*New Tools for Dermatological Diagnosis. Journal of Biomedical Optics* 3(1): 21-31). In TD-OCT, the optical path length between the sample and reference arms needs to be mechanically scanned.

FD-OCT may be either swept source OCT (SS-OCT) or spectrometer based spectral domain OCT (SD-OCT). In both SS-OCT and SD-OCT, the optical path length difference between the sample and reference arm is not mechanically scanned. Instead, a full axial scan (also called A-scan) is obtained in parallel for all points along the sample axial line within a short time determined by the wavelength sweep rate of the swept source (in SS-OCT) or the line scan rate of the line scan camera (in SD-OCT). As a result, the speed for each axial scan can be substantially increased as compared to the mechanical scanning speed of TD-OCT.

The location of the fovea is clinically important because it is the locus of highest visual acuity. Automated analyses of retinal thickness are ideally centered about the fovea, with peripheral regions of diminishing importance further from the fovea.

FD-OCT's improved scanning rates enable the rapid acquisition of data with minimal or correctable motion artifacts. Recent emergence of SD-OCT within the field of ophthalmology increases the information available to automatically detect foveal location than was present in TD-OCT datasets.

There is limited previous work in the area of automatic foveal identification for OCT. Previous work on scanning laser tomography [Li et al.] has looked at retinal topography as one method to determine foveal location, but this is prone to disruption by pathology. Other work on foveal identification from fundus photos [Niemeijer et al., Narasimha-Iyer et al.] benefits from the presence of the Optic Nerve Head as a landmark in the image, which is not generally available in OCT images of the macula at the present state of the art.

The present invention satisfies the need for improved methods for automatically processing OCT data and identifying the fovea.

SUMMARY

The present invention is defined by the claims and nothing in this section should be taken as a limitation on those claims. Advantageously, embodiments of the present invention overcome the lack of fovea identification processing for OCT data.

The fovea has a number of distinguishing anatomical characteristics that may be used to identify it in OCT images. The most evident feature of a healthy fovea is the indentation of the Inner Limiting Membrane (ILM), although the presence of pathology such as edema or posthyaloid membrane traction may disrupt the normal foveal topography. Additionally, the inner retinal layers are thinner near the fovea, and the inner and outer plexiform layers normally pinch together toward the ILM in this region. The fovea has a higher proportion of cone photoreceptors than the surrounding retina, and their relatively long outer segments can cause a peak in the highly reflective boundary between the inner and outer photoreceptor segment layers at the fovea. This anatomy can, of course, be disrupted by a variety of outer-retinal pathologies.

Another distinguishing characteristic is that the vasculature emanating from the Optic Nerve Head (ONH) does not extend into the fovea. This is presumably because the vessels would obscure the dense population of photoreceptors that provide acute central vision.

Our invention applies a cost function to various measurements, attributes of measurements, or other information derived from an OCT volume scan. Our method allows the incorporation of different types of information into a cost function, from which the fovea is automatically detected.

BRIEF DESCRIPTION OF THE DRAWINGS

FIG. 6 (a) is an en-face image formed from integrating a slab volume taken below the ILM.

FIG. 6 (b) is an image of an example ILM slab contribution to a cost function.

FIG. 6 (c) is an image of an example blood vessel component contribution to a cost function.

FIG. 6 (d) is an image of an example automatically detected fovea.

DETAILED DESCRIPTION

Figure 1:
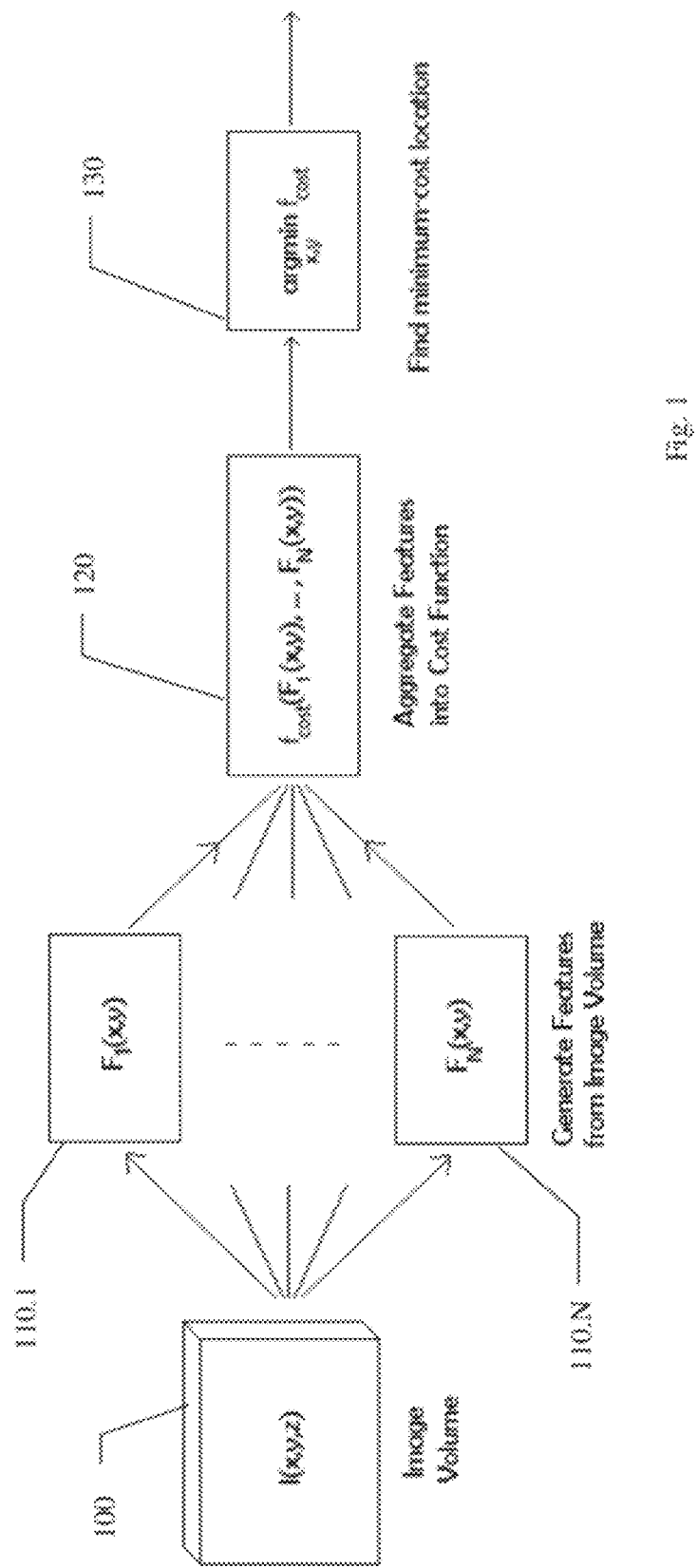
FIG. 1 is a functional diagram for developing a cost function.

The image analysis primarily seeks a lateral location characterized by a relatively low reflectivity just below the ILM.

Avoiding vascularized regions and/or biasing the decision toward the scan center aids in the identification of the fovea. A cost function is defined containing terms from separate analyses of sub-ILM reflectivity and vessel and scan location, and the fovea is determined as the location of minimum cost.

A simple cost function C(x,y) can be expressed as:

$$C(x,y) = c_1((R*S)(x,y)) + c_2\sqrt{x^2+y^2} \qquad (Eq. 1)$$

Where x and y are lateral coordinates, S(x, y) is an en-face image of the OCT volume (from a partially-integrated fundus projection, for example), R(x,y) is a radially symmetric filter such as the top-hat filter, (R*S) is the convolution of the image with the filter, $\sqrt{x^2+y^2}$ is the usual distance metric, and $c_1$ and $c_2$ are constants chosen to weight the convolution and distance appropriately. In this case, the cost function chooses the point closest to the origin that has the most radially symmetric neighborhood. Since typically OCT volumes are acquired with the fovea near the center of the en-face image, Equation 1 is generally more viable with the origin of the co-ordinate system located at the center of the en-face image.

Alternatively, the cost function $$C(x,y,u,v) = c_1((R*S)(x,y)) + c_2\sqrt{(x-u)^2+(y-v)^2} \qquad (Eq. 2)$$

may be used. Here the location (u, v) is constrained to vary over locations expected to be near the center of the fovea. This requires additional computational power for evaluating the minimum over a four dimensional space rather than a two dimensional space, but reduces the dependency on the operator acquiring data in the traditional manner.

In general, a cost function could be any linear or nonlinear combination of location dependent terms that increases as the likelihood of the location being at or near the center of the fovea decreases. For example, the distance function could be squared in either Equation 1 or 2. Alternatively, instead of using a radial filter on the en-face image, the factor or factors may be extracted from tomographic data in the image volume. It is known that the distance from the Internal Limiting Membrane (ILM) to the Inner Plexiform Layer (IPL) is normally a minimum in the neighborhood of the center of the fovea, so the cost function may include a measure of the distance from the ILM to the IPL. Because of the difficulties involved in segmenting the IPL, it is likely that another measure of local depression of the ILM would be used, such as a measure of local curvature or the deviation from a best fit ellipsoidal surface. The cost function could also include a measure of the retinal thickness as measured by the distance from ILM to Retinal Pigment Epithelium (RPE) or a measure of the vasculature of the region, since this distance also is normally a minimum in the neighborhood of the center of the fovea. The cost function may include any combination of these or other factors, or any function of factors, so long as the resulting cost function attains its minimum either at or near the center of the fovea. This cost function architecture combines various types of information contained in the image volume to be extracted from the volume image and combined to locate the center of the fovea.

FIG. 1 illustrates the typical architecture for determining the center of the fovea using a cost function methodology. Features 110.1 to 110.N are extracted from the image volume 100 and converted to measures $F_1(x, y)$ to $F_N(x, y)$ which attain their minimum at or near the location (x, y) at the center of the fovea. The feature measures are weighted and combined 120 to create the cost function, whose minimum is determined 130 to find the location of the center of the fovea.

In this case, the cost function may look like:

$$C(x,y) = \sum_{k=1}^{N} c_k F_k(x,y) \qquad (Eq. 3)$$

or $$C(x,y) = \prod_{k=}^{N} F_k^{c_k}(x,y) \qquad (Eq. 4)$$

or other combinations of the individual measures which preserve the minimum of the cost function at or near the center of the fovea.

Figure 2:
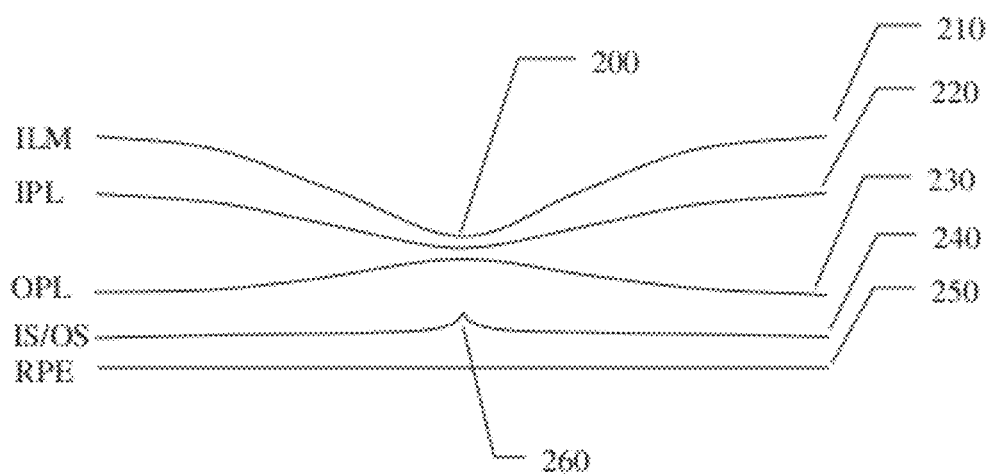
FIG. 2 is an idealized illustration of the key retinal boundary layers in the region of the fovea.

FIG. 2 illustrates the boundary layers at the fovea from a tomographic perspective. This idealized sketch illustrates some important features of the retinal layers. This illustration shows the narrowing of the gap between the ILM 210 and the IPL 220 in the vicinity of the foveal center 200. Similarly, the gap between the ILM 210 and the Outer Plexiform Layer (OPL) 230 narrows in the vicinity of the foveal center, as does the gap between the IPL 220 and the OPL 230. The peak 260 in the boundary of the Inner and Outer Segments of photoreceptors (IS/OS) 240 is caused by the relatively long cone photoreceptors of the IS/OS in the neighborhood of the foveal center. In a healthy retina, the RPE 250 is a relatively flat boundary layer and this illustration shows that the distance from the RPE to the ILM or IPL layers achieves a minimum either at or near the foveal center, while the distance from the RPE to the OPL achieves a maximum at the foveal center. Any number of these measurements can be used as measures contributing to the cost function.

The weights $c_k$ in the cost function may be pre-computed from theory, determined empirically or computed as part of the analysis preceding the formation of the cost function. For example, if two measures $F_1$ and $F_2$ each attain their minimum at the foveal center, but the average noise of $F_1$ is twice that of $F_2$, then a cost function $$C(x,y) = 0.5 \times F_1(x,y) + F_2(x,y) \qquad (Eq. 5)$$

theoretically balances the noise from the two measurements. Alternatively, the relative weights of the cost function may be determined empirically from data by evaluating the minimum of the cost function for a plurality of choices of the weights and choosing those weights which provide the best estimate of the foveal center. Finally, during data analysis, it might be determined that for this data, one particular measure cannot be trusted and the weight applied to that measure can be set to zero so that the untrusted measurement does not influence the estimate of the location of the foveal center. Alternatively, that measurement might be included, but only with a very small weight, so that its influence in incremental, but not dominating.

It should be noted that the vasculature in the neighborhood of the Optic Nerve Head (ONH) does not extend into the fovea. Hence, the blood vessel structure can also be used as a guide to finding the fovea. One useful measure here is the distance from a location to the nearest blood vessel. Of course, this measure requires a feature identification process for identifying blood vessels. This measure also achieves a local maximum (not a minimum) at or near the foveal center for most eyes. One function that is minimal at or near the foveal center is the reciprocal of this distance.

Figure 3:
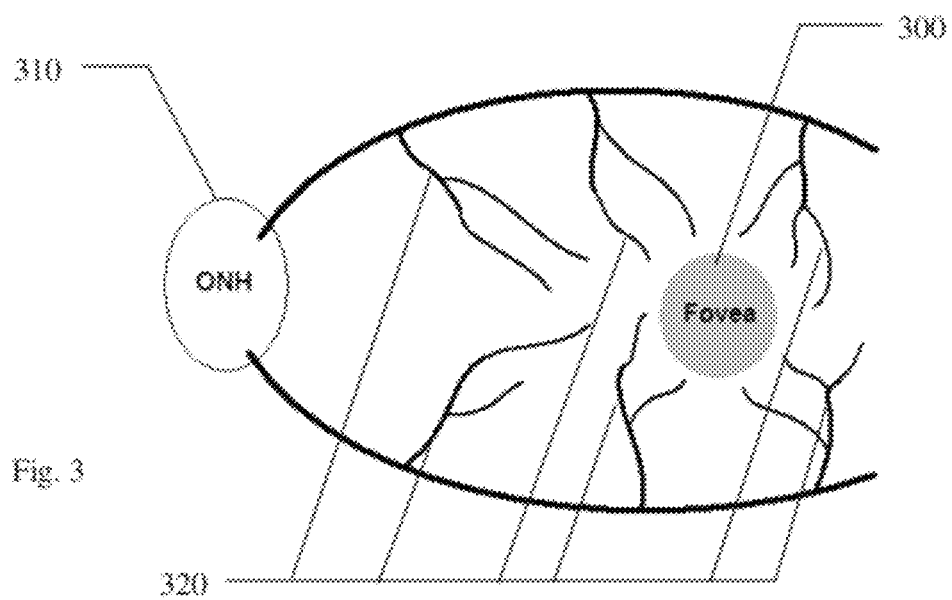
FIG. 3 is an idealized illustration of the vascular regions in the neighborhood of the fovea and the optic nerve head.

FIG. 3 is an idealized illustration of the vascular regions in the neighborhood of the fovea 300 and the optic nerve head 310. Blood vessels 320 do not extend into the region of the fovea and the center of the fovea is some distance from the nearest blood vessel.

Determining the foveal center using a cost function approach is distinct from approaches that may make preliminary hard decisions and then arbitrate among those preliminary choices.

Figure 4:
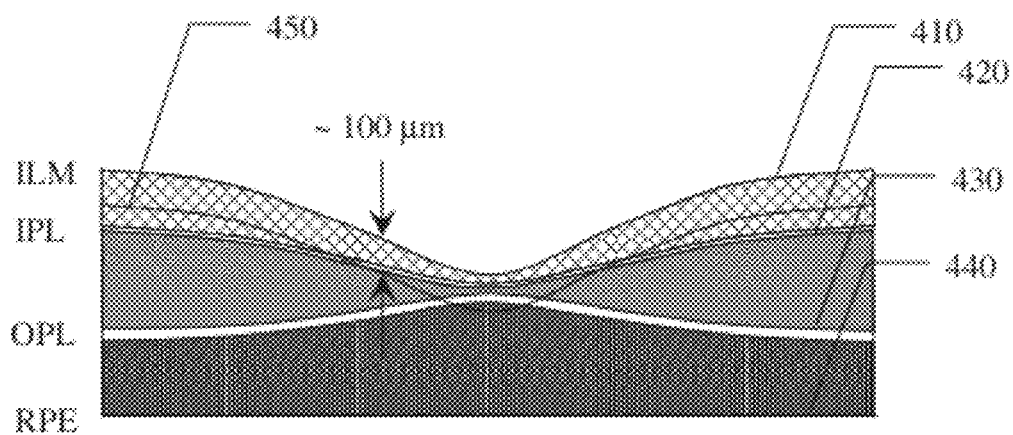
FIG. 4 is an idealized illustration of the layers included in an example ILM slab, shown from a tomographic view.

FIG. 4 illustrates one measure useful in creating a cost function, either alone or in combination with other feature measures. The illustration is an idealized tomographic view of the retinal layers. This view emphasizes the variations of the tissue reflectivity between layers and over depth. An en-face image is created by summing the intensity data that represents depth reflectivity. Using a segmentation of the ILM surface as an input, we create a volume (slab) and analyze the intensity of the image volume at each lateral location. The intensity is summed in depth starting at the ILM 410 and extending approximately a fixed distance 450 below the ILM (in this example the distance is chosen to be about 100 microns). Since the tissue in the upper regions between layers is generally more reflective than the tissue in the deeper regions and the layers are thinnest near the foveal center, this sum will achieve its minimum value at or near the center of the fovea. In general, the region between the ILM 410 and the IPL 420 is brighter than the region between the IPL 420 and the OPL 430, which is in turn brighter than the region from the OPL 430 to the RPE 440.

Figure 5:
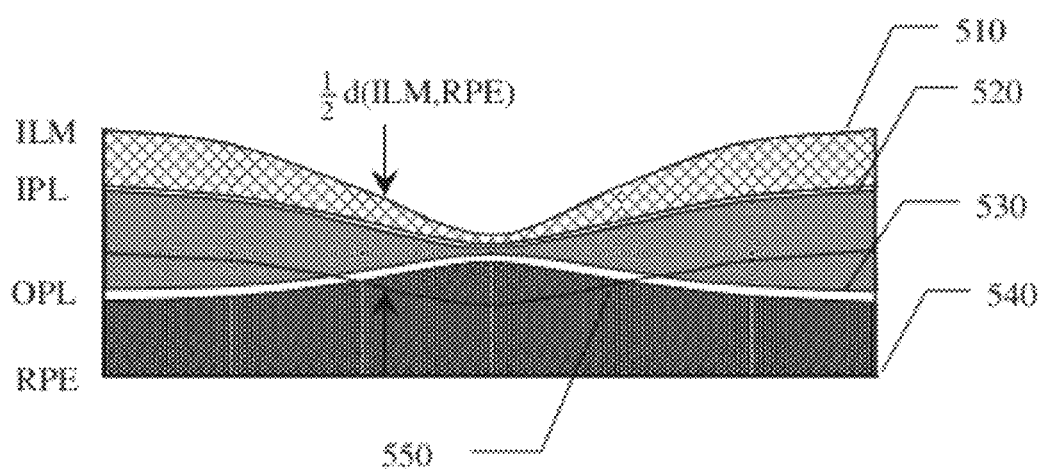
FIG. 5 is an idealized illustration of the layers included in an alternative example ILM slab, shown from a tomographic view.

FIG. 5 illustrates an alternative measure. Again, the illustration is an idealized tomographic view of the retinal layers. In this instance, instead of summing the intensity from the ILM over a fixed depth to create the en-face image, the intensity is summed from the ILM 510 to the midpoint 550 between the ILM and RPE. When surface 550 is between the OPL 530 and the RPE 540, this sum includes the intensity from the ILM 510, IPL 520 and OPL 530, and the regions between these layers, as well as a region below the OPL 530 and above the RPE 540. This summed en-face intensity image directly includes intensity information from the thinned regions near the foveal center as well as including fewer points in the sum near the foveal center because of the nature of the foveal pit. The intensity in this depth window corresponds to a partial-volume projection of the data [Ref. U.S. Pat. No. 7,301,644, Knighton, et al.], but other measures of reflectivity may also be used to similar effect.

The reflectivity analysis (sometimes called an en-face image) of the volume of image data (sometimes called a slab) just below the ILM achieves a minimum (a dark spot) at the location of a normal fovea. This occurs because the inner retina thins in the vicinity of the fovea, and the ILM also dips down at this point, so that some of the darker layers of the retina appear in the band a fixed distance below the ILM. Although pathology or imaging artifacts may disrupt the dark spot or cause the appearance of other dark spots in the sub ILM slab intensity, a robust method for detection of this dark spot can locate the fovea well, especially when aided by other information such as vasculature, scan location, or the circularity of the dark spots.

Radially symmetric linear or nonlinear filters such as the Laplacian, Mexican-hat, or top-hat filters are ideal for this application. Since the diameter of the fovea is about 1 mm, the lateral window of the analysis of reflectivity is ideally somewhat less than 1 mm, but should be large enough to exclude artifacts. A top-hat linear filter with 375 microns inner radius and 750 microns outer radius gave good results.

A second term in the cost function seeks to locate the foveal avascular zone. Vessel-enhanced images [Frangi et al.; Sato et al.] may be formed from partial-volume projections of the OCT data. The vessel image can be smoothed to create an additional term for the cost function. A separate embodiment thresholds and dilates the image to create a mask that narrows down the possible locations of the fovea. A distance transformation of the vessel image has previously been used in estimating fovea locations in scanning laser tomography images. [Li et al.]

For example, FIG. 6 shows (a) an ILM slab, (b) the ILM slab reflectivity component of the cost function, (c) the blood vessel component of the cost function, and (d) is an ILM slab image including indicia (in this case, a small circle) overlaid over the image, displaying the computed location of the fovea. The location of the fovea was automatically determined in this example using a cost function composed of terms representing the slab reflectivity and the locations of blood vessels within the eye.

A term related to distance (only minimal for maximum distances) may be weakly used in the cost function such as the lateral distance from the scan center. This relies on the assumption that the fovea is located near the center of the scan, which is generally true. The typical protocol for data collection is designed so that the fovea is within the image cube and substantially separate from the volume boundaries.

Other terms may be included in the cost function, using information such as the depth of the ILM surface or the thickness of the outer segment of the photoreceptors.

The cost function may be modified based on an assessment of the quality of its inputs. If the sub-ILM slab appears to be free from artifacts, the supplementary information from the vessel-enhanced image may be de-emphasized or excluded entirely. Also, if the quality of the vessel-enhanced image is deemed to be poor, the method may substitute the distance from the scan center as a supplementary term.

In some cases, the cost function may be used in conjunction with reasoning to make the solution more robust. It is well known that measurement noise is inherent in every measuring technique. Speckle can be viewed as noise in OCT measurements, since it generally contains no useful information. Speckle is an image artifact that is due to subresolution scatterers. Either because of the speckle itself or because of the analytic techniques applied to the data to minimize the effects of speckle, the location of the absolute minimum of the cost function may not be the center of the fovea. Hence, it is useful to augment the cost function with additional reasoning, such as a binary classifier or a machine learning technique to add robustness to the solution.

For example, we can perform a histogram of the cost function results and fix a threshold that includes only a small percentage of the data (say 1%). Rather than only choosing the minimum as the solution, we select all points within the threshold of the minimum as potential solutions. We analyze the potential solutions to select the foveal center. We map the potential solutions and then process the map using various image analysis tools. Since the entire region about the foveal center should be nearly minimal in the cost function, there should be a region about the foveal center in the mapping of the thresholded data. We may erode this map to remove isolated pixels. We connect neighboring regions using the morphological operations of dilation and erosion. The foveal center will be a fairly circular elliptical region some distance from any edge of the image. (The foveal pit is nearly circular and, for the typical exam, should be well within the image boundaries.) We can apply another cost function to the connected regions to select the most elliptical region that is furthest from the image boundary.

The threshold need not be chosen to be 1% of the data. 0.5% or 2% may be used, or in cases where image levels are well calibrated, a fixed threshold may be used. Of fundamental importance is that a significant majority of the data points are eliminated as potential locations of the foveal center.

Once the fovea is found, its location can be used for a variety of applications. The location can simply be displayed for the user to shown as shown in FIG. 6(d) or stored for future use. The location can also be temporarily or fleetingly stored and used in the computation of another value or parameter, such as the measurement of the macular thickness. The location of the fovea is used to center the bulls-eye fields of the nine subfield grid (similar to the macular grid of the Early Treatment Diabetic Retinopathy Study). The central subfield (center disc of the bulls-eye) is properly centered on the foveal center. A common measure of retinal thickness is the central subfield thickness. However, locating the fovea also provides the location of the Inner Ring Macular Thickness and Outer Ring Macular Thickness. Measurements of the Inner and Outer rings, as well as their Superior, Inferior, Temporal and Nasal subfields, are also used for evaluating retinal health.

In addition, the location of the fovea can be used as an input for a segmentation algorithm. A layer such as the IS/OS which is generally difficult to segment can be more easily segmented when even an approximate location of the fovea is known. Alternatively, iterative techniques may use an approximate segmentation of a layer to get an initial estimate of the location of the fovea, which in turn is used to get a better segmentation of the layer, which can then be used to get a better estimate of the location of the fovea.

Alternatively, the location of the fovea can be used as an input for a registration algorithm. Disease progression measurement is dependent on repeated measurements performed at the same location at different times. The location of the fovea can be used as a fixed point to register two images of the same eye taken at different times or using different modalities. When comparing images taken at different times, the foveal location can be stored with the original image, stored in a location associated with the original image, stored in a patient report, or otherwise stored so as to be available for use on the return visit. Such storage may be fleeting, as in local memory storage for use in further analysis. Alternatively, the foveal location can be recomputed from the volume data at the time that it is needed.

In conjunction with the location of the optic disc, the location of the fovea can be used to determine how the anatomy of a specific eye affects the correlation between measured structure and measures of visual field function. That is, these two locations are key in locating the actual path of the nerve fibers within the eye. Since the nerve fiber pathways are slightly different in each eye, the measurement of the locations of the optic disc and the fovea can be instrumental in mapping these fiber pathways and correlating structure to function.

Figure 7:
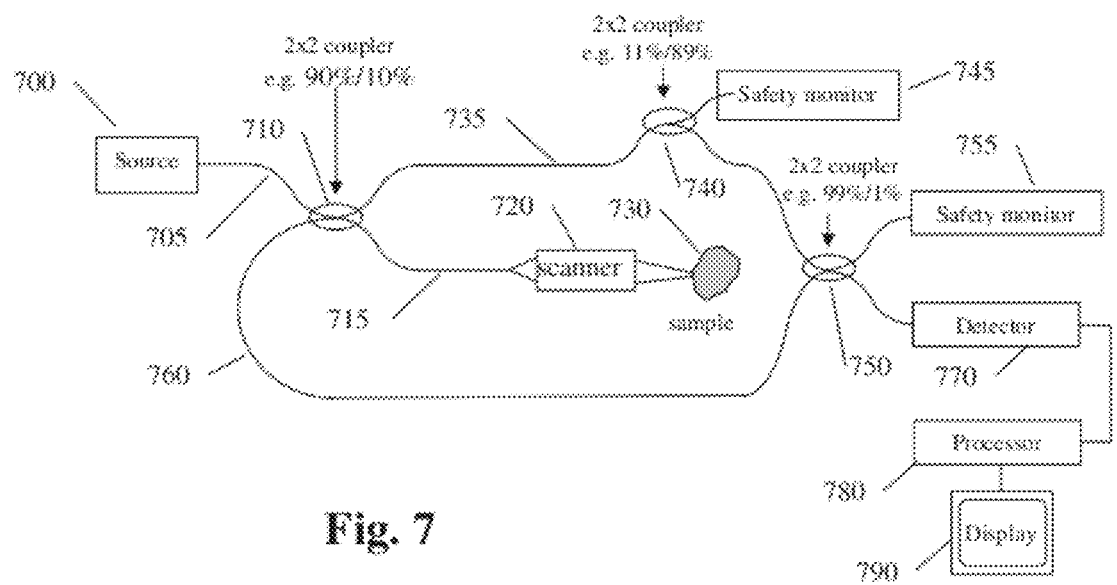
FIG. 7 illustrates one design of an optical coherence tomography system.

FIG. 7 illustrates an OCT device which can be used to implement the subject invention. Further information about this type of OCT device is disclosed in U.S. Patent Publication No. 2007/0291277, incorporated herein by reference. A low coherence light source 700, typically a superluminescent diode (SLD), is coupled to source fiber 705 that routes light to directional coupler 710. The optimal directional strength of the coupling depends on system design choices and may be 90/10 (as shown in FIG. 7) or 70/30 or other choices depending on SLD back reflection tolerance, the source illumination required to image the sample and other system design parameters. Directional coupler 710 splits the light into sample fiber 715 and reference fiber 735. The sample path may include a delay apparatus (not shown) to adjust the length of the sample path. The transverse scanner 720 deflects the OCT beam and preferably creates a focus in the beam near the region of interest in sample 730. The transverse scanner laterally scans the optical beam across the sample in order to image a volume of the sample.

Some light scattered from sample 730 returns through the scanner and delay apparatus to sample fiber 715. Coupler 710 routes this light through loop 760 to fiber coupler 750, where it interferes with the reference light. The combining coupler 750 provides two outputs. These outputs can be used for balanced detection (see U.S. Pat. No. 5,321,501 FIG. 10). Alternatively, the coupling ratio of coupler 750 can be adjusted to send most of the interfered light to a single OCT detector 770. Each OCT detector can be a single photodetector for use in time-domain OCT or swept-source OCT, or a spectrometer for use in spectral domain OCT.

Optional tap 740 diverts a fraction of the reference light to detector 745, which may be used to monitor the source power. Monitoring may be included to monitor the safety of the sample or to detect a degradation in the source 700. Alternatively, monitoring may not be included at all in the system. The tap removes some fraction of optical power from the reference fiber 735, reducing the power that reaches coupler 750. Sensitivity in OCT can reach the shot-noise limit if the reference power is large enough to bring the interference signal above receiver noise, but not so large as to bring intensity noise or beat noise above the level of shot noise.

The coupling ratios in directional couplers 710, 740 and 750 are chosen to set a safe level of illumination to the sample, and to set the appropriate reference power at the detector or detectors. For example, in the case of ophthalmic OCT of the retina using light with wavelengths near 850 nm, the safe exposure level is approximately 0.5 mW, and the optimum reference level at the detector is approximately 0.005 mW. Sources are available in this wavelength range having output power of approximately 5 mW. For these conditions one would use a coupling ratio near 90%/10% in the splitting coupler 710 so that 10% of the source power reaches the sample. 90% of the scattered light will then be routed to loop 760. In the case where there is a single OCT detector 770, the combining coupler 750 preferably routes most of the sample light to that detector. The splitting coupler routes 90% of source light, 4.5 mW, to reference fiber 735, while only 0.005 mW is required at the detector. One could use a combining coupler 750 that couples 0.1% of the reference light into the single OCT detector 770, but in manufacture it is difficult to control the 0.1% coupling factor. A preferred solution is to use a 99%/1% split ratio in combining coupler 750, and take advantage of the additional degree of freedom in tap 740 to adjust the reference power. Nominally, tapping 89% of the power form reference fiber 735 will provide an appropriate reference level of 0.005 mW at OCT detector 770, in this example.

As an alternative to adjusting the tap ratio of optional tap 740, one can adjust the reference level by including attenuating fiber (U.S. Pat. No. 5,633,974) in the reference path.

The output of the detector 770 is routed to processor 780. This processor may be a single device or a plurality of devices, preferentially optimized for their portion of processing. The processor 780 is connected to one or more peripherals providing a user interface devices, such as display 790. Display 790 can be used to generate images of the type shown in FIG. 6d. The processor might also be connected to other user interface devices (such as a keyboard, mouse, joystick, and others), and one or more external communication devices (such as a USB or network connector, optical storage media, printer, internet, and others), as well as possibly connecting to other imaging hardware (such as cameras, fixation targets, fundus viewers, and others) or peripheral patient devices (such as head support, height adjustment, and others) which are not shown. The processor 780 provides the computational power (in one or more modules) processing functions such as image formation, volume rendering, segmentation, registration, evaluation of cost functions, and/or other computational tasks required for medical imaging and analysis.

It should be understood that the embodiments, examples and descriptions have been chosen and described in order to illustrate the principles of the invention and its practical applications and not as a definition of the invention. Modifications and variations of the invention will be apparent to those skilled in the art. For example, while SD-OCT systems are the most likely implementation, similar performance SS-OCT systems are expected to achieve similar results and even TD-OCT systems can be used, with degraded performance. The scope of the invention is defined by the claims, which includes known equivalents and unforeseeable equivalents at the time of filing of this application.

The following references are hereby incorporated herein by reference.

US Patent Documents

U.S. Pat. No. 7,301,644, Knighton, et al., "Enhanced optical coherence tomography for anatomical mapping"
2007/0291277, Everett; Matthew J., et al., "Spectral domain optical coherence tomography system"

Other Publications

A. Frangi, W. Niessen, R. Hoogeveen, T. van Walsum, and M. Viergever, "Model-based quantitation of 3D magnetic resonance angiographic images," IEEE Trans. Med. Imag., vol. 18, no. 10, pp. 946-956, October 1999.
Y. Li, N. Hutchings, and J. G. Flanagan, "Automated Detection of the Retinal Blood Vessels and Fovea for Scanning Laser Tomography Images", Invest. Ophthalmol. Vis. Sci. 48: E-Abstract 2605 (2007).
Sato Y, Nakajima S, Shiraga N, Atsumi H, Yoshida S, Koller T, Gerig G, and Kikinis R, "Three dimensional multi-scale line filter for segmentation and visualization of curvilinear structures in medical images", Medical Image Analysis, 2(2): 143-168, 1998.
M. Niemeijer, B. van Ginneken, F. ter Haar, M. D. Abramoff, "Automatic detection of the optic disc, fovea and vascular arch in digital color photographs of the retina", in: Proceedings of the British Machine Vision Conference, Editor(s): W. F. Clocksin, A. W. Fitzgibbon, P. H. S. Torr, 2005, pp. 109-118.
M. Niemeijer, M. D. Abramoff, B. van Ginneken, "Segmentation of the optic disc, macula and vascular arch in fundus photographs", IEEE Transactions on Medical Imaging, 2007, vol. 26, pp. 116-127.
Narasimha-Iyer, H., Can, A., Roysam, B., Stewart, V., Tanenbaum, H. L., Majerovics, A., Singh, H., "Robust detection and classification of longitudinal changes in color retinal fundus images for monitoring diabetic retinopathy", IEEE Transactions on Biomedical Engineering vol. 53, no. 6, pp. 1084-1098 (June 2006)
Leitgeb, R. A., et al., (2003). "Performance of fourier domain vs. time domain optical coherence tomography." Optics Express 11:889-894;
de Boer, J. F. et al., (2003). "Improved signal-to-noise ratio in spectral-domain compared with time-domain optical coherence tomography." Optics Letters 28: 2067-2069;
Choma, M. A., et al., (2003). "Sensitivity advantage of swept source and Fourier domain optical coherence tomography." Optics Express 11: 2183-2189
Hitzenberger, C. K., et al. (1998). "In-vivo intraocular ranging by wavelength tuning interferometry". Coherence Domain Optical Methods in Biomedical Science and Clinical Applications II, SPIE.
Häusler, G. and M. W. Lindner (1998). "'Coherence Radar' and 'Spectral Radar'—New Tools for Dermatological Diagnosis." Journal of Biomedical Optics 3(1): 21-31

What is claimed is:

1. An apparatus for generating 3D image information from within the eye of a patient and for identifying the location of the fovea from within the image information, said apparatus comprising:

an optical coherence tomography (OCT) system, said system including a light source, a beam splitter for dividing the light along a sample arm and a reference arm, said sample arm further including a scanner for scanning the beam transversely over the eye, said OCT device including a detector for receiving light returned from both the sample and the reference arms and generating signals corresponding to three dimensional image information based on a reflection distribution as a function of depth arising from reflecting features in the eye; and a processor for segmenting the image information and assigning a single representative intensity value for each transverse location across the segmented region wherein the representative intensity value corresponds to an integrated intensity as a function of depth across the segmented region and determining the location of the fovea based on the transverse location having a minimum representative intensity value.

2. An apparatus are recited in claim 1 further including a display for displaying the image information and the determined foveal location.

3. An apparatus as recited in claim 1 wherein the segmented region corresponds to a region beginning at the inner limiting membrane (ILM) and extending to a predetermined depth below the ILM.

4. An apparatus as recited in claim 1 wherein the processor evaluates a second, different foveal location dependent image quantity that reaches an extremum as the likelihood of that location being at or near the center of the fovea increases and wherein the results of the evaluation of the second different foveal location dependent image quantity are used to improve the determination of the location of the fovea.

5. An apparatus as recited in claim 1 wherein said processor determines the location of the blood vessels in the image information and utilizes the blood vessel location information to improve the determination of the location of the fovea.

6. An apparatus as recited in claim 1 wherein when determining the location of the fovea, the processor further considers the lateral distance from the center of the scanned region in the plane of the scan.

7. An apparatus as recited in claim 1 wherein said processor determines the thickness of the macular layer in the region of the determined foveal location.

8. An apparatus as recited in claim 1 wherein the segmented region corresponds to a region beginning at the inner limiting membrane (ILM) and extending to a depth below the ILM, said depth being determined as a function of the distance from the ILM to the retinal pigment epithelium (RPE).

9. An apparatus for generating 3D image information from within the eye of a patient and for identifying the location of the fovea from within the image information, said apparatus comprising:

an optical coherence tomography (OCT) system, said system including a light source, a beam splitter for dividing the light along a sample arm and a reference arm, said sample arm further including a scanner for scanning the beam transversely over the eye, said OCT device including a detector for receiving light returned from both the sample and the reference arms and generating signals corresponding to three dimensional image information based on a reflection distribution as a function of depth arising from reflecting features in the eye; and a processor for segmenting the image information to isolate a region wherein the integrated intensity of the image information within the segmented region reaches a minimum as the likelihood of that location being at or near the center of the fovea increases, said integrated intensity being computed as a function of depth, said processor analyzing the integrated intensity image information to determine the location where the intensity has reached a minimum to determine the foveal location.

10. An apparatus are recited in claim 9 further including a display for displaying the image information and the determined foveal location.

11. An apparatus as recited in claim 9 wherein the segmented region corresponds to a region beginning at the inner limiting membrane (ILM) and extending to a predetermined depth below the ILM.

12. An apparatus as recited in claim 9 wherein the segmented region corresponds to a region beginning at the inner limiting membrane (ILM) and extending to a depth below the ILM, said depth being determined as a function of the distance from the ILM to the retinal pigment epithelium (RPE).

13. An apparatus as recited in claim 9 wherein the processor evaluates a second, different foveal location dependent image quantity that reaches an extremum as the likelihood of that location being at or near the center of the fovea increases and wherein the results of the evaluation of the second different foveal location dependent image quantity are used to improve the determination of the location of the fovea.

14. An apparatus as recited in claim 9 wherein said processor determines the location of the blood vessels in the image information and utilizes the blood vessel location information to improve the determination of the location of the fovea.

15. An apparatus as recited in claim 9 wherein when determining the location of the fovea, the processor further considers the lateral distance from the center of the scanned region in the plane of the scan.

16. An apparatus as recited in claim 9 wherein said processor determines the thickness of the macular layer in the region of the determined foveal location.

17. An apparatus for generating 3D image information from within the eye of a patient and for identifying the location of the fovea from within the image information, said apparatus comprising:

an optical coherence tomography (OCT) system, said system including a light source, a beam splitter for dividing the light along a sample arm and a reference arm, said sample arm further including a scanner for scanning the beam transversely over the eye, said OCT device including a detector for receiving light returned from both the sample and the reference arms and generating signals corresponding to three dimensional image information based on a reflection distribution as a function of depth arising from reflecting features in the eye; and a processor analyzing the image information to determine the location of the fovea within the image, said analyzing step including evaluating a quantity associated with each of at least two different independent indicators of foveal location, said two different indicators being combined and weighted, wherein one of said indicators of foveal location relates to the level of integrated intensity across the image, said integrated intensity being measured as a function of depth.

18. An apparatus as recited in claim 17 wherein the integrated intensity is evaluated in a region the near inner limiting membrane (ILM).

19. An apparatus as recited in claim 17 wherein one of said indicators of foveal location relates to the location of blood vessels in the image information.

20. An apparatus as recited in claim 17 wherein the relative weighting of the indicators is adjusted based on the level of noise associated with the respective measurements.

21. An apparatus are recited in claim 17 further including a display for displaying the image information and the determined foveal location.

22. An apparatus as recited in claim 17 wherein said processor determines the thickness of the macular layer in the region of the determined foveal location.

* * * * *

UNITED STATES PATENT AND TRADEMARK OFFICE
CERTIFICATE OF CORRECTION

| | | |
|---|---|---|
| PATENT NO. | : 8,251,511 B2 | |
| APPLICATION NO. | : 13/299962 | |
| DATED | : August 28, 2012 | |
| INVENTOR(S) | : Paul F. Stetson et al. | |

It is certified that error appears in the above-identified patent and that said Letters Patent is hereby corrected as shown below:

On first page, field (54) and Column 1, line 2, in "Title", delete "SDOCT" and insert -- SD-OCT --, therefor.

In column 10, line 34, in claim 2, delete "are recited" and insert -- as recited --, therefor.

In column 11, line 20, in claim 10, delete "are recited" and insert -- as recited --, therefor.

In column 12, line 30, in claim 18, delete "the" and insert -- to the --, therefor.

In column 12, line 38, in claim 21, delete "are recited" and insert -- as recited --, therefor.

Signed and Sealed this
Sixth Day of November, 2012

David J. Kappos
*Director of the United States Patent and Trademark Office*